US010571478B2

(12) United States Patent
Paczesny

(10) Patent No.: US 10,571,478 B2
(45) Date of Patent: Feb. 25, 2020

(54) BIOMARKERS AND ASSAY TO DETECT CHRONIC GRAFT VERSUS HOST DISEASE

(71) Applicant: Indiana University Research and Technology Corporation, Indianapolis, IN (US)

(72) Inventor: Sophie Paczesny, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 109 days.

(21) Appl. No.: 15/529,595

(22) PCT Filed: Nov. 23, 2015

(86) PCT No.: PCT/US2015/062166
§ 371 (c)(1),
(2) Date: May 25, 2017

(87) PCT Pub. No.: WO2016/085866
PCT Pub. Date: Jun. 2, 2016

(65) Prior Publication Data
US 2017/0261518 A1 Sep. 14, 2017

Related U.S. Application Data

(60) Provisional application No. 62/084,077, filed on Nov. 25, 2014.

(51) Int. Cl.
*G01N 33/53* (2006.01)
*G01N 33/68* (2006.01)
*C07K 16/18* (2006.01)
*C07K 16/24* (2006.01)
*C07K 14/52* (2006.01)
*C07K 14/54* (2006.01)

(52) U.S. Cl.
CPC ......... *G01N 33/6893* (2013.01); *C07K 16/18* (2013.01); *C07K 16/24* (2013.01); *G01N 33/53* (2013.01); *G01N 33/6863* (2013.01); *G01N 33/6869* (2013.01); *C07K 16/244* (2013.01); *G01N 2333/522* (2013.01); *G01N 2333/7155* (2013.01); *G01N 2333/95* (2013.01); *G01N 2333/96486* (2013.01); *G01N 2800/245* (2013.01); *G01N 2800/52* (2013.01)

(58) Field of Classification Search
CPC .. A61K 38/00; A61K 38/1709; A61K 38/177; A61K 38/18; A61K 38/20; A61K 38/195; C07K 14/47; C07K 14/54; C07K 14/71; C07K 14/522; C07K 14/7155; C07K 14/435; G01N 33/6845; G01N 33/68; G01N 33/6863; G01N 2333/52; G01N 2333/522; G01N 2333/96494; G01N 33/6893

See application file for complete search history.

(56) References Cited

U.S. PATENT DOCUMENTS

2013/0115232 A1 5/2013 Ferrara et al.
2013/0287772 A1 10/2013 Halbert et al.
2017/0336409 A1* 11/2017 Richards .......... G01N 33/56911

OTHER PUBLICATIONS

Jin et al. Kidney injury molecule-1 and osteopontin: new markers for prediction of early kidney transplant rejection. Mol Immunol 54: 457-464, 2013.*
Ka et al. Glomerular crescent-related biomarkers in a murine model of chronic graft versus host disease. Nephrol Dial Transplant 21: 288-298, 2006.*
Kitco et al. MIG: a plasma chronic GVHD biomarker that is diagnostic at onset and associated with disease severity. Bone Marrow Transplant 48(Suppl2): s45, Apr. 2013.*
Paczesny, S. Discovery and validation of graft-versus-host disease biomarkers. Blood 121(4): 585-594, 2013.*
Pidala et al. Biologic markers of chronic GVHD. Bone Marrow Transplant 49: 324-331, 2014 (published online Jul. 22, 2013).*
Ponce et al. High day 28 ST2 biomarker levels predict severe day 100 acute graft-versus-host disease and day 180 transplant-related mortality after double-unit cord blood transplantation. Blood 122: 146, 2013.*
Rosenberg et al. A role for MMP-3 in the modulation of early T cell responses in GVHD. Blood 122: 3258, 2013.*
Salmela et al. Overexpression of tissue inhibitor of metalloproteinases-3 in intestinal and cutaneous lesions of graft-versus-host disease. Mod Pathol 16(2): 108-114, 2003.*
Wang et al. Osteopontin level correlates with acute cellular renal allograft rejection. J Surg Res 182: 161-165, 2013.*
Yu et al. Biomarker panel for chronic graft-versus-host disease. J Clin Oncol 34(22): 2583-2590, 2016.*
Ariail et al.,Oral Graft-versus-Host Disease: correlation between histopathology and salivary inflammatory mediators, 2013, pp. 1-3, no journal citation provided.
Kitko et al., Plasma CXCL9 elevations correlate with chronic GVHD diagnosis; Blood, 2014, vol. 123, No. 5, pp. 786-793.
Vander Lugt et al., ST2 as a Marker for Risk of Therapy-Resistant Graft-versus-Host Disease and Death, The New England Journal of Medicine, 2013, pp. 529-539.
Paczesny et al., Graft-versus-Host Disease biomarkers omics and personalized medicine, 2013, vol. 98, No. 3, pp. 275-292.
Ponce et al., High day 28 ST2 levels predict for acute graft-versus-host disease and transplant-related mortality after cord blood transplantation, Blood, 2015, vol. 125, No. 1, pp. 199-206.
Ross et al., Multiplexed Protein Quantitation in *Saccharomyces cerevisiae* Using Amine-reactive Isobaric Tagging Reagents, Molecular & Cellular Proteomics, vol. 3, No. 12, 2004, pp. 1154-1169.
Zhao et al., Blockade of osteopntin reduces alloreactive CDE8+ T cell-mediated graft-versus-Host disease, BLOOD, 2011, vol. 117, No. 5, pp. 1723-1733.

(Continued)

Primary Examiner — Bridget E Bunner
(74) Attorney, Agent, or Firm — Barnes & Thornburg LLP

(57) ABSTRACT

A four-biomarker panel for diagnosis of chronic graft-versus-host disease (cGVHD) and methods of prognosing and/or diagnosing cGVHD using the biomarker panel are disclosed.

5 Claims, 7 Drawing Sheets

(56) References Cited

OTHER PUBLICATIONS

Nejmoa 1213299 Appendix: Supplementary Appendix, Supplement to : Vander Lugt MT et al., "St2 as a marker for risk of therapy-resistant graft-versus-host disease and death," N Engl J Med 2013; 369:529-39. DOI: 10.1056/NEJMoa1213299.
Exhibit A: ST2/IL-33R: Products: R&D Systems, https://www.mdsystems.com/products/mouse-sl2-il-33r-antibody-245707_mab10041; downloaded Jul. 16, 2019, 8 pages.
Exhibit B: Mouse ST2/IL-33R Antibody MAB10041-100: R&D Systems, ttps://www.rndsystems.com/target/st2-il-33r; downloaded Jul. 16, 2019, 10 pages.
Exhibit C: ST2 Suppression of tumorgenicity 2 [*Homo sapiens* (human)]; https://www.ncbi.nlm.nih.gov/gene/6761, downloaded Apr. 16, 2019, 3 pages.
Miller et al., "Soluble ST2 Associates with Diabetes But Not Established Cardiovascular Risk Factors: A New Inflammatory Pathway of Relevance to Diabetes?", PLOS One, wwwplosone.org, Oct. 2012, vol. 7, Issue 10, e47830.
Miller review: Miller, A.M., "Role of IL-33 in inflammation and disease," Journal of Inflammation, 2011, 8:22 (12 pages).
Snyder and Sundberg: Snyder et al., "Molecular Interactions in Interleukin and Toll-like Receptor Signaling Pathways," Current Pharmaceutical Design, 2014, 20, 1244-1258.
Zeisbrich et al., "Transplant-Associated Renal Microangiopathy is Associated with a High Risk of Refractory Gvhd and Characterized by a Specific Biomarker Signature," www.bloodjournal.org/content/124/21/3909.abstract, 6 pages, Blood 124: 3909, 2014.

\* cited by examiner

BIOMARKERS AND ASSAY TO DETECT CHRONIC GRAFT VERSUS HOST DISEASE

CROSS-REFERENCE TO RELATED APPLICATIONS

This application claims priority to International Application Number PCT/US2015/062166, filed on 23 Nov. 2015, which claims priority to U.S. Provisional Patent Application Ser. No. 62/084,077 filed on Nov. 25, 2014, both of which are hereby incorporated by reference in their entireties.

STATEMENT OF GOVERNMENT SUPPORT

This invention was made with government support under CA174667, DK090948, CA118953, CA163438 awarded by the National Institutes of Health. The Government has certain rights in the invention.

BACKGROUND OF THE DISCLOSURE

The present disclosure is generally directed to a biomarker panel for diagnosis of chronic graft-versus-host disease (cGVHD) and to methods of diagnosing cGVHD using the biomarker panel. Particularly, the biomarker panel is a four-biomarker panel including ST2, CXCL9, MMP3, and OPN.

Chronic graft-versus-host disease (cGVHD) remains the major contributor to morbidity and mortality for survivors of allogeneic hematopoietic cell transplant (HCT), reportedly occurring in 30-70% of adults and children surviving more than 100 days. It is also the leading cause of non-relapse mortality (NRM) occurring more than 2 years after the HCT for malignant disease. cGVHD usually starts more than 3 months after a transplant, and can last a lifetime. Chronic symptoms may include: dry eyes or vision changes; dry mouth, white patches inside the mouth, and sensitivity to spicy foods; fatigue, muscle weakness, and chronic pain; joint pain or stiffness; skin rash with raised, discolored areas, as well as skin tightening or thickening; shortness of breath; vaginal dryness; and weight loss.

cGVHD occurs in allogeneic bone marrow transplantation recipients when donor immune cells recognize the host tissues as foreign and attack them. This reaction can be minimized by carefully matching the donor and host tissues and using prophylactic immunosuppression, but it is still one of the leading causes of morbidity and mortality for survivors of allogeneic hematopoietic cell transplant. Pre-transplant clinical or transplant characteristics have minimal ability to predict GVHD outcomes. Currently, cGVHD is diagnosed by clinical symptoms using the NIH chronic GVHD consensus criteria as set forth in National Institutes of Health Consensus Development Project on Criteria for Clinical Trials in Chronic Graft-versus-Host Disease: I. The 2014 Diagnosis and Staging Working Group report, Jagasia et al., Biol. Blood Marrow Transplant, 2015, 21(3):389-401. Particularly, for diagnosis, the following criteria must be met: (1) distinction from acute GVHD; (2) presence of at least 1 diagnostic clinical sign of chronic GVHD or presence of at least 1 distinctive manifestation confirmed by pertinent biopsy or other relevant tests; and (3) exclusion of other possible diagnoses. Therefore, at the time of diagnosis, patients can already have substantial organ damage.

Despite multiple clinical trials investigating innovative treatments for cGVHD, the standard treatment for the last 30 years remains predominantly steroids, with or without calcineurin inhibitors, that is incompletely effective, is associated with infections and long-term risks of toxicity. Accordingly, there has been a push in the art to develop biomarker immunoassays for conclusive GVHD diagnosis before the onset of symptoms, because in the event that a patient develops GVHD, it is critically important to treat them early to prevent organ damage.

BRIEF DESCRIPTION OF THE DISCLOSURE

The present disclosure is generally directed to a biomarker panel including four biomarkers (ST2, CXCL9, MMP3, and OPN) with ELISA for providing an accurate diagnosis of CGVHD.

Accordingly, in one aspect, the present disclosure is directed to a diagnostic biomarker panel comprising IL-1RL1 (also known as ST2), chemokine ligand 9 (CXCL9), matrix metalloproteinase-3 (MMP3), and osteopontin (OPN).

In another aspect, the present disclosure is directed to a method of diagnosing or of aiding diagnosis of chronic graft-versus-host disease (cGVHD) in a subject receiving hematopoietic cell transplantation (HCT). The method comprises: measuring in a biological sample from the subject the expression of a biomarker panel comprising IL-1RL1 (also known as ST2), chemokine ligand 9 (CXCL9), matrix metalloproteinase-3 (MMP3), and osteopontin (OPN) by contacting the biological sample obtained from the subject with at least a first agent that specifically binds to ST2, at least a second agent that specifically binds to CXCL9, at least a third agent that specifically binds to MMP3, and at least a fourth agent that specifically binds to OPN, wherein each specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of cGVHD.

In another aspect, the present disclosure is directed to a method of prognosing or of aiding prognosis of chronic graft-versus-host disease (cGVHD) in a subject receiving hematopoietic cell transplantation (HCT). The method comprises: measuring in a biological sample from the subject the expression of a biomarker panel comprising IL-1RL1 (also known as ST2), chemokine ligand 9 (CXCL9), matrix metalloproteinase-3 (MMP3), and osteopontin (OPN) by contacting the biological sample obtained from the subject with at least a first agent that specifically binds to ST2, at least a second agent that specifically binds to CXCL9, at least a third agent that specifically binds to MMP3, and at least a fourth agent that specifically binds to OPN, wherein each specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of a prognosis for a subject having cGVHD.

BRIEF DESCRIPTION OF THE DRAWINGS

FIG. 6A depicts ROC curves for the combination model in verification cohort 2 comparing (i) patients on prednisone at time of sampling (dotted line) with cGVHD (n=51) v. time-matched controls on prednisone without cGVHD (n=22): AUC 0.65; (ii) patients not on prednisone at time of sampling (solid line) with cGVHD (n=36) v. time-matched controls not on prednisone without cGVHD (n=71): AUC 0.77. FIG. 6B depicts ROC curves for the combination model in the verification cohort 2 comparing (i) patients with cGVHD and with prior acute GVHD (dotted line) (n=36) v. time-matched controls without cGVHD but with prior acute GVHD (n=45): AUC 0.7; (ii) patients with cGVHD, but without prior acute GVHD (solid line) (n=47) v. time-matched controls without cGVHD and without prior acute GVHD (n=44): AUC 0.80.

DETAILED DESCRIPTION OF THE DISCLOSURE

Figure 1:
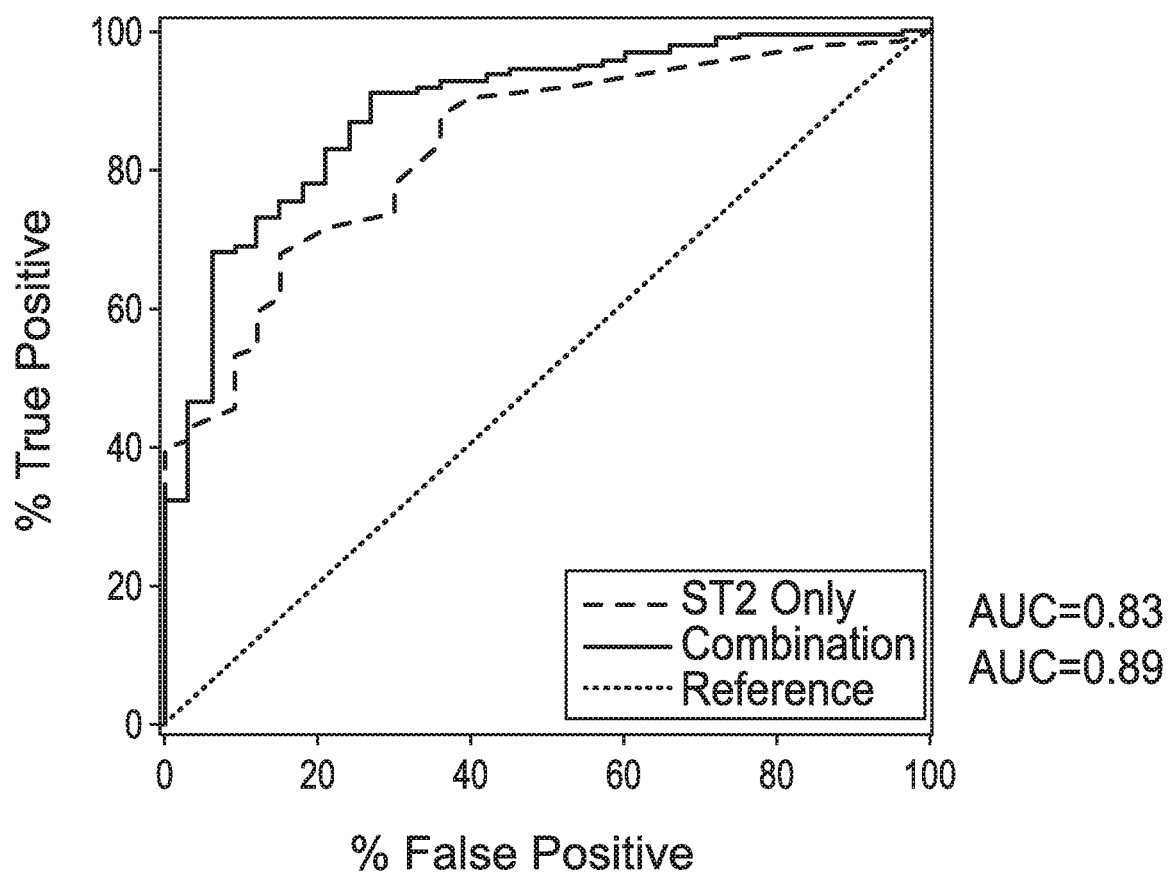
FIG. 1 depicts ROC curves for the best single biomarker and the combination model in verification cohort 1 as analyzed in Example 1. Particularly, ROC curves for the best single biomarker (ST2, dotted line, AUC=0.83) and the combination model (solid line, AUC=0.89).

The present disclosure generally relates to a multi-biomarker panel for reliable, non-invasive diagnosis of cGVHD. The identified markers represent several pathways, including inflammatory, T cell trafficking, cutaneous fibroblast activation, endothelial injury, and tissue remodeling. Particularly, it has been discovered herein that IL 1RL1 (also known as ST2), chemokine ligand 9 (CXCL9), matrix metalloproteinase-3 (MMP3), and osteopontin (OPN) can be employed in biomarker panels to diagnosis cGVHD. Further, in one embodiment, a biomarker panel can be employed to provide opportunities for preemptive intervention to minimize the incidence and severity of cGVHD clinical symptoms, and thereby increase survival. The present disclosure further relates to the use of these biomarkers and biomarker panels for prognosing, diagnosing, and/or treating cGVHD in a subject that has received allogeneic hematopoietic cell transplant (HCT).

The present disclosure uses examples to disclose the invention and also to enable any person skilled in the art to practice the invention, including making and using any panels or devices and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Unless otherwise defined, all terms of art, notations and other scientific terminology used herein are intended to have the ordinary meanings commonly understood by those of ordinary skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

A. Definitions

As used herein, the term "biomarker" refers to an indicator of, for example, a pathological state of a subject, which can be detected in a biological sample of the subject. Biomarkers include DNA-based, RNA-based and protein-based molecular markers.

As used herein, the term "diagnosis" refers to the identification or classification of a molecular or pathological state, disease or condition. For example, "diagnosis" can refer to identification of a particular type of a condition (such as chronic graft-versus host disease ("cGVHD")).

As used herein, the term "aiding diagnosis" refers to methods that assist in making a clinical determination regarding the presence, or nature, of a particular type of symptom or condition of a condition (such as cGVHD). For example, a method of aiding diagnosis of a condition (such as cGVHD) can include measuring the expression of certain genes in a biological sample from an individual.

As used herein, the term "prognosis" is used herein to refer to the categorization of patients by degree of risk for a disease (such as cGVHD) or progression of such disease. A "prognostic marker" refers to an assay that categorizes patients by degree of risk for disease occurrence or progression.

As used herein, the term "sample" refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. A "tissue" or "cell sample" refers to a collection of similar cells obtained from a tissue of a subject or patient. The source of the tissue or cell sample may be blood or any blood constituents (e.g., whole blood, plasma, serum) from the subject. The tissue sample can also be primary or cultured cells or cell lines. Optionally, the tissue or cell sample is obtained from a disease tissue/organ. The tissue sample can contain compounds which are not naturally intermixed with the tissue in nature such as preservatives, anticoagulants, buffers, fixatives, nutrients, antibiotics, and the like.

As used herein, the terms "control", "control cohort", "reference sample", "reference cell", "reference tissue", "control sample", "control cell", and "control tissue" refer to a sample, cell or tissue obtained from a source that is known, or believed, to not be afflicted with the disease or condition for which a method or composition of the present disclosure is being used to identify. The control can include one control or multiple controls. In one embodiment, a reference sample, reference cell, reference tissue, control sample, control cell, or control tissue is obtained from a healthy part of the body of the same subject or patient in whom a disease or condition is being identified using a composition or method of the present disclosure. In one embodiment, a reference sample, reference cell, reference tissue, control sample, control cell, or control tissue is obtained from a healthy part of the body of an individual who is not the subject or patient in whom a disease or condition is being identified using a composition or method of the invention.

The term "antibody" is used in its broadest sense and specifically covers, for example, monoclonal antibodies, polyclonal antibodies, antibodies with polyepitopic specificity, single chain antibodies, multi-specific antibodies and fragments of antibodies. Such antibodies can be chimeric, humanized, human and synthetic.

The term "subject" is used interchangeably herein with "patient" to refer to an individual to be treated. The subject is a mammal (e.g., human, non-human primate, rat, mouse, cow, horse, pig, sheep, goat, dog, cat, etc.). The subject can be a clinical patient, a clinical trial volunteer, an experimental animal, etc. The subject can be suspected of having or at risk for having a condition (such as cGVHD) or be diagnosed with a condition (such as cGVHD). According to one embodiment, the subject to be treated according to this invention is a human.

As used herein, "treating", "treatment" and "alleviation" refer to measures, wherein the object is to prevent or slow down (lessen) the targeted pathologic condition or disorder or relieve some of the symptoms of the disorder. Those in need of treatment can include those already with the disorder as well as those prone to have the disorder, those at risk for having the disorder and those in whom the disorder is to be prevented.

"Elevated expression level" and "elevated levels" refer to an increased expression of a mRNA or a protein in a patient (e.g., a patient suspected of having or diagnosed as having cGVHD) relative to a control, such as subject or subjects who are not suffering from cGVHD.

B. Methods of Prognosing

In one embodiment, the present disclosure is directed to a method of prognosing or of aiding in the prognosis of cGVHD in a subject receiving hematopoietic cell transplantation (HCT). The method comprises:

obtaining a biological sample from the subject;

measuring in a biological sample from the subject the expression of a biomarker panel comprising IL-1RL1 (also known as ST2), chemokine ligand 9 (CXCL9), matrix metalloproteinase-3 (MMP3), and osteopontin (OPN) by contacting the biological sample obtained from the subject with at least a first agent that specifically binds to ST2, at least a second agent that specifically binds to CXCL9, at least a third agent that specifically binds to MMP3, and at least a fourth agent that specifically binds to OPN, wherein each specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of a prognosis for shortened survival compared to median survival in a subject having cGVHD, and wherein a reduced biomarker expression level compared to biomarker expression obtained from a biological sample obtained from a control is indicative of a prognosis for increased survival compared to median survival in a subject having cGVHD.

The specific binding agent can be selected from a nucleic acid, an antibody, a receptor, and a lectin.

The sample can be selected from tissue, whole blood, plasma and serum.

The specific binding agent-biomarker complex can be detected using methods known to those skilled in the art such as, for example, microarray analysis, immunoassay, immunohistochemistry, and mass spectrometry. Representative immunoassays include Western blot analysis and ELISA.

It has been advantageously found that the biomarker panels used in the methods of the present disclosure can be used for prognosing cGVHD early after HCT. Particularly, in some embodiments, the methods can be used to prognose cGVHD as early as 180 days from HCT, and in some embodiments, as early as 100 days from HCT. Accordingly, the methods of prognosing cGVHD can include obtaining the biological sample at day 100 from HCT, including obtaining the sample from day 100 to day 180 from HCT.

C. Methods of Diagnosing

In another embodiment, the present disclosure is directed to a method for diagnosing cGVHD in a subject, particularly a subject receiving hematopoietic cell transplantation. The method comprises:

measuring in a biological sample from the subject the expression of a biomarker panel comprising IL-1RL1 (also known as ST2), chemokine ligand 9 (CXCL9), matrix metalloproteinase-3 (MMP3), and osteopontin (OPN) by contacting the biological sample obtained from the subject with at least a first agent that specifically binds to ST2, at least a second agent that specifically binds to CXCL9, at least a third agent that specifically binds to MMP3, and at least a fourth agent that specifically binds to OPN, wherein each specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of cGVHD.

The specific binding agent can be selected from a nucleic acid, an antibody, a receptor, and a lectin.

The sample can be selected from tissue, whole blood and plasma.

The specific binding agent-biomarker complex can be detected using methods known to those skilled in the art such as, for example, microarray analysis, immunoassay, immunohistochemistry, and mass spectrometry. Representative immunoassays include Western blot analysis and ELISA.

It has been advantageously found that the biomarker panels used in the methods of the present disclosure can be used for diagnosing cGVHD early after HCT. Particularly, in some embodiments, the methods can be used to diagnose cGVHD as early as day 100 from HCT, including obtaining the sample as early as day 180 from HCT, and including from day 100 to day 180 from HCT.

G. Biological Sample

The biological sample used in the methods of the present disclosure can be obtained using certain methods known to those skilled in the art. Biological samples may be obtained from vertebrate animals, and in particular, mammals. In certain instances, a biological sample is tissue, whole blood, plasma, or serum. By screening such body samples, a prognosis or diagnosis can be achieved for cGVHD.

As used in the various methods of the present disclosure, the terms "control", "control value", "reference" and "reference value" refer to an expression level value obtained from control sample", "control cell", and "control tissue" "reference sample", "reference cell", and "reference tissue" obtained from a source that is known, or believed, to not be afflicted with the condition for which a method or composition is being used to identify. It is to be understood that the control need not be obtained at the same time as the biological sample of the subject is obtained. Thus, a control value for an expression level can be determined and used for comparison of the expression level for the biological sample of the subject or the biological samples of multiple subjects.

H. Detection of Biomarkers

Expression levels of proteins may be detected in samples of tissue, whole blood, or serum. Various methods are known in the art for detecting protein expression levels in such biological samples, including various immunoassay methods.

Example 1

In this Example, mass spectrometry-based proteomic analysis was conducted to compare plasma pooled from onset of 17 patients with de novo cGVHD, from onset of 18 patients with progressive cGVHD, and matched time-point samples from 18 patients without GVHD.

Methods

Patients and Samples

Three cohorts of patients were included in this Example (cGVHD discovery, cGVHD verification cohort 1, and cGVHD verification cohort 2). Heparinized blood samples were collected prospectively at the onset of manifestations in patients with chronic GVHD or at matched time points in controls. In addition to being scored at each institution, redacted medical records were retrospectively reviewed by one clinician and one data manager with expertise in cGVHD, who confirmed that cases met the NIH consensus criteria for diagnosis of the disease and had active GVHD at the time of sample collection, while the controls had no signs or symptoms of GVHD.

Proteomics

Sample Preparation and Protein Fractionation

Figure 8:
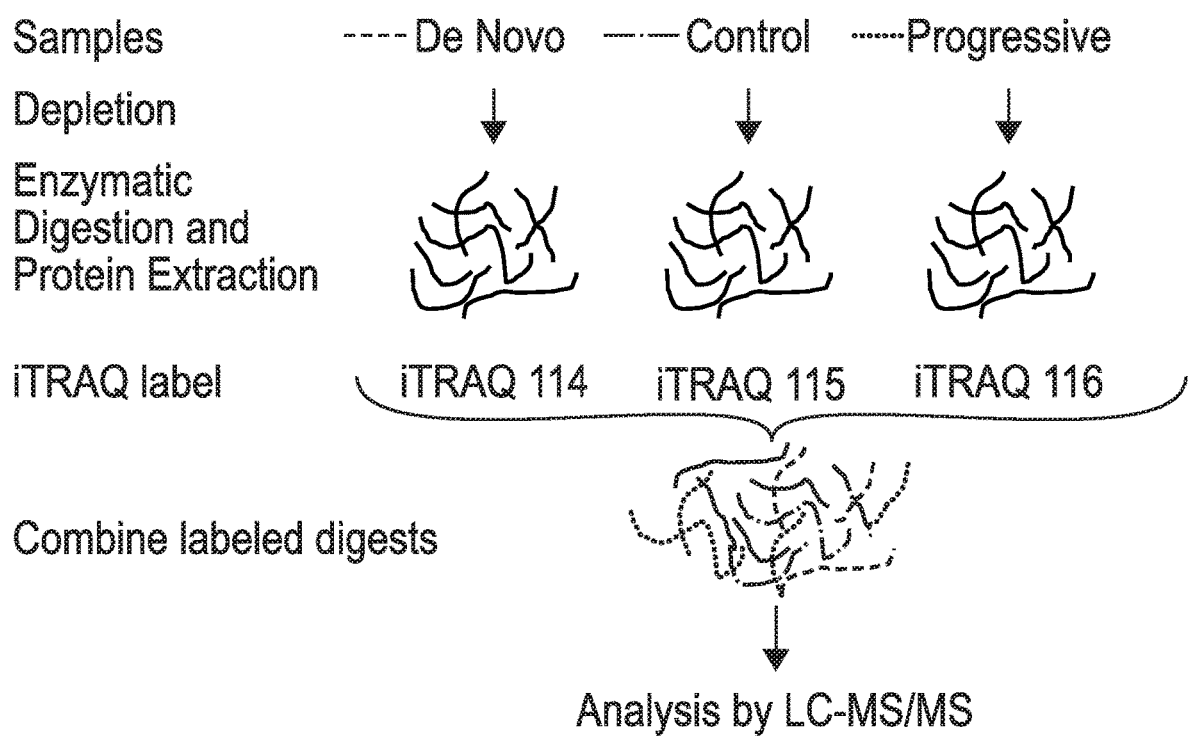
FIG. 8 depicts the iTRAQ proteomics workflow in Example 1.

Three pools of plasma were compared in the same proteomic experiment to discover biomarkers of cGVHD. Pool 1 contained plasma from 17 patients with de novo cGVHD, available at the onset of clinical symptoms, pool 2 contained plasma from 18 controls without cGVHD (collected at a similar time point as cGVHD samples), and pool 3 contained plasma from 18 patients with progressive cGVHD. The overall proteomics workflow is shown in FIG. 8.

Each pool contained 25 µl of plasma. The three pooled plasma samples were then individually immunodepleted of the 20 common hyper-abundant proteins with a PROTEOPREP®20 plasma immunodepletion kit (Sigma-Aldrich, St. Louis, Mo.) according to manufacturer's protocol. The flow-through fractions (depleted plasma) were then concentrated using VIVASPIN® 500 (Viva products, Inc., Littleton, Mass.). After measuring protein concentrations of depleted and concentrated plasma with a Micro BCA protein assay reagent kit (ThermoFisher Scientific, Waltham, Mass.), 50-µg aliquots were precipitated using acetone at −20° C. overnight. After centrifugation for 20 minutes at 15,000×g, acetone was decanted, and the air-dried protein pellets were dissolved in 25 µL of 1.0 M triethylammonium bicarbonate, 1 µL of 2% sodium dodecyl sulfate (SDS), and 2 µL of 50 mM tris-(2-carboxyethyl) phosphine (TCEPP) provided in an iTRAQ® reagents application kit (as described by Ross et al., Molecular & cellular proteomics: MCP, 2004; 3(12): 1154-69)—plasma and incubated for 1 hour at 60° C. Cysteine residues were alkylated by adding 1 µL of 84 mM iodoacetamide in water to each vial and incubating for 30 minutes in darkness. All samples were trypsinized by adding 10 µg trypsin (Sigma-Aldrich, St. Louis, Mo.) in 10 µL water and incubating them overnight at 37° C. Each pool was labeled with a different tag allowing for differential quantification. Three iTRAQ reagents, 114-116, were added in 70 µL ethanol to each vial along with 10 µL sample buffer plasma to adjust the pH to greater than 8, and the vials were incubated at room temperature for 1 hour. The samples were labeled in the following order: 1) de novo cGVHD with label 114, 2) control with label 115, and 3) progressive cGVHD with label 116. The labeling reaction was quenched by adding 100 µL water and incubating the tubes for 30 minutes at room temperature. All vials were dried in a speed vac separately and stored at −20° C. until fractionation by strong cation-exchange (SCX) chromatography.

The three pooled plasma samples were dissolved in buffer A (7 mM potassium phosphate, 30% acetonitrile, pH 2.65) and combined immediately before fractionation with a SCX column (Zorbax 300-SCX 5 µm, 2.1×150 mm, Agilent). The sample pH was adjusted to less than 3 with 2% trifluoroacetic acid (TFA). Fractions were collected at 1 minute intervals at a flow rate of 200 µL/minute from 1% solvent B (7 mM potassium phosphate, 500 mM KCl, 30% acetonitrile, pH 2.65) to 60% over 40 minutes (1% B for 7 minutes, 6-15% B for 23 min, 15-34% B for 15 minutes, and 34-60% B for 10 minutes) as well as during column washing with 98% solvent B for 10 minutes. The chromatographic elution was monitored using a UV detector at λ=220 nm. These fractions were consolidated into 20 fractions using the UV trace to distribute the peptide quantities similarly. After drying them in a speed vac, peptides were desalted using SEP-PAK® C18 (50 mg) cartridges. The cartridges were conditioned with 1 mL acetonitrile, 2×1 mL of 65% acetonitrile in 0.1% TFA in water followed by 2×1 mL of 0.1% TFA. After sample loading in 1 mL of 0.1% TFA and 2 washes with 1 mL of 0.1% TFA, peptides were eluted using 1 mL of 65% acetonitrile in 0.1% TFA in water and dried in a speed vac.

LC-MS/MS Analysis

LC-MS/MS analysis was performed with an Easy-nLC 1000 (Thermo Scientific, Waltham, Mass.) coupled to an Orbitrap Elite mass spectrometer (Thermo Scientific). The LC system configured in a vented format consisted of a fused-silica nanospray needle (PicoTip™ emitter, 75 μm ID, New Objective, Inc., Woburn, Mass.) packed in-house with 25 cm of Magic C18 AQ 100 Å reverse-phase media (Michrom Bioresources Inc., Auburn, Calif.), and a trap (IntegraFrit™ Capillary, 100 μm ID, New Objective, Inc., Woburn, Mass.) containing 2 cm Magic C18 AQ 200 Å. The peptide sample was diluted in 30 μL of 2% acetonitrile and 0.1% formic acid in water, and injection volumes ranging between 4-8 μL were loaded onto the column in triplicate and separated using a two-mobile-phase system consisting of 0.1% formic acid in water (A) and 0.1% formic acid in acetonitrile (B). A 90-minute gradient from 7% to 35% B at a flow rate of 400 nL/minute was used for chromatographic separation. The mass spectrometer was operated in a data-dependent MS/MS mode over the m/z range of 400-1800. The precursor scan mass resolution was set to 60,000. For each cycle, the 10 most abundant ions from the precursor scan were selected for MS/MS analysis using 40% normalized HCD collision energy and analyzed in the orbitrap with the resolution set to 15,000. Selected ions were dynamically excluded for 45 seconds.

Peptide and Protein Identification from Mass Spectra of Digested Fragments

The acquired LC-MS/MS data were analyzed using two approaches. In the first approach, Proteome Discoverer™ version 1.4 was used for data analysis. The MS/MS data were searched against the Swiss-Prot human proteome database (release 2012_01, 74127 entries) using SEQUEST with the following parameters: trypsin was set as the digestion protease, with 2 maximum missed cleavages; precursor and fragment error tolerance were 10 part per million (ppm) and 0.6 Dalton, respectively; iTRAQ modification of N-termini was a fixed modification; and iTRAQ modification of lysine residues, carbamidomethyl on cysteine residues, and oxidation of methionine residues as variable modifications. Identified peptides were filtered according to a 1% peptide-level false discovery rate (FDR) using Percolator. Proteins with at least one identified peptide were reported.

In the second approach, the mass spectra were searched against the same database using Mascot™ version 2.4 with the same parameters as used in the first approach. Identified proteins were then filtered with the significance threshold p<0.05 and at least one identified peptide.

The mass spectrometry proteomics data have been deposited in the ProteomeXchange Consortium via the PRIDE partner repository with the dataset identifier PXD002762.

ELISA

Validation of the proteins of interest from the proteomics analysis was performed with a sequential ELISA protocol to maximize the number of measured analytes per sample by reusing the same aliquot consecutively in individual ELISA plates. Commercial antibody pairs were available for 22 proteins (Table 1), and ST2 and CXCL9 ELISAs were performed as previously reported (Kitko et al., Blood. 2014; 123(5):786-93; Ponce et al., Blood. 2015; 125(1):199-205). Samples and standards were analyzed in duplicate according to a previously described protocol (Paczesny et al., Blood. 2009; 113(2): 273-8; Vander et al., The New England journal of medicine. 2013; 369(6): 529-39; Fiema et al., Journal of visualized experiments: JoVE. 201268).

TABLE 1

Twenty-two proteins selected from the proteomics discovery

| Protein | Description | Commercial ELISA provider | Plasma dilution | LLOD | ULOD |
|---|---|---|---|---|---|
| ACAN | aggrecan | R&D DuoSet | 1/3 | 125 pg/mL | 8000 pg/mL |
| CD44 | CD44 molecule | eBioscience | 1/60 | 125 pg/mL | 4000 pg/mL |
| CDH5/VE cadherin | cadherin 5, type 2 (vascular endothelium) | R&D Quantikine | 1/100 | 1.56 ng/mL | 100 ng/mL |
| COMP | cartilage oligomeric matrix protein | R&D Quantikine | 1/100 | 0.16 ng/mL | 10 ng/mL |
| ECM1 | extracellular matrix protein 1 | SinoBiological | 1/2000 | 0.023 ng/mL | 1.5 ng/mL |
| ENG/CD105 | endoglin | R&D DuoSet | 1/50 | 125 pg/mL | 8000 pg/mL |
| FAP | fibroblast activation protein, alpha | R&D DuoSet | 1/100 | 62.5 pg/mL | 4000 pg/mL |
| FCN3 | ficolin (collagen/fibrinogen domain containing) 3 | Hycult | 1/150 | 7.8 ng/mL | 500 ng/mL |
| FN1 | fibronectin 1 | eBioscience | 1/20000 | 0.31 ng/mL | 20 ng/mL |
| HSP90a | Heat shock protein 90 alpha | Enzo Life Sience | 1/25 | 0.063 ng/mL | 4 ng/mL |
| ICOSLG | inducible T-cell co-stimulator ligand | SinoBiological | 1/30 | 0.063 ng/mL | 4 ng/mL |
| C-KIT | v-kit Hardy-Zuckerman 4 feline sarcoma viral oncogene homolog | Cell Sciences | 1/15 | 0.31 ng/mL | 10 ng/mL |

TABLE 1-continued

Twenty-two proteins selected from the proteomics discovery

| Protein | Description | Commercial ELISA provider | Plasma dilution | LLOD | ULOD |
|---|---|---|---|---|---|
| LAMP1 | lysosomal-associated membrane protein 1 | SinoBiological | 1/100 | 15.6 pg/mL | 1000 pg/mL |
| MCAM/CD146 | melanoma cell adhesion molecule | SinoBiological | 1/250 | 0.078 ng/mL | 5 ng/mL |
| MMP3 | matrix metalloproteinase 3 (stromelysin 1) | R&D Duoset | 1/25 | 31.2 pg/mL | 2000 pg/mL |
| NCAM1/CD56 | neural cell adhesion molecule 1 | R&D DuoSet | 1/200 | 78.1 pg/mL | 5000 pg/mL |
| POSTN | periostin, osteoblast-specific factor | R&D DuoSet | 1/25 | 0.36 ng/mL | 24 ng/mL |
| SELL/CD62L | selectin L | R&D Duoset | 1/200 | 78.1 pg/mL | 5000 pg/mL |
| SELP | selectin P | R&D Duoset | 1/50 | 125 pg/mL | 8000 pg/mL |
| SPP1/OPN | osteopontin/secreted phosphoprotein 1 | R&D Duoset | 1/25 | 62.5 pg/mL | 4000 pg/mL |
| TGFBI | transforming growth factor, beta-induced, 68 kDa | R&D DuoSet | 1/1000 | 62.5 pg/mL | 4000 pg/mL |
| TNFRSF10C/TRAILR3 | tumor necrosis factor receptor superfamily, member 10c, decoy without an intracellular domain | R&D DuoSet | 1/25 | 62.5 pg/mL | 4000 pg/mL |

LLOD: lower limit of detection;
ULOD: upper limit of detection

Statistical Analysis

Clinical differences in the groups with and without cGVHD were compared with Student's t tests for continuous variables and with Fisher's exact tests for categorical variables. Logistic regression was used to evaluate the associations between cGVHD and biomarkers after log transformation. All analyses were adjusted for significant clinical variables considering age, sex, stem cell source, conditioning (myeloablative v. others), donor (matched sibling v. others), and time from HCT to sample collection, and in one instance, for steroid use in verification cohort 2.

Figure 4:
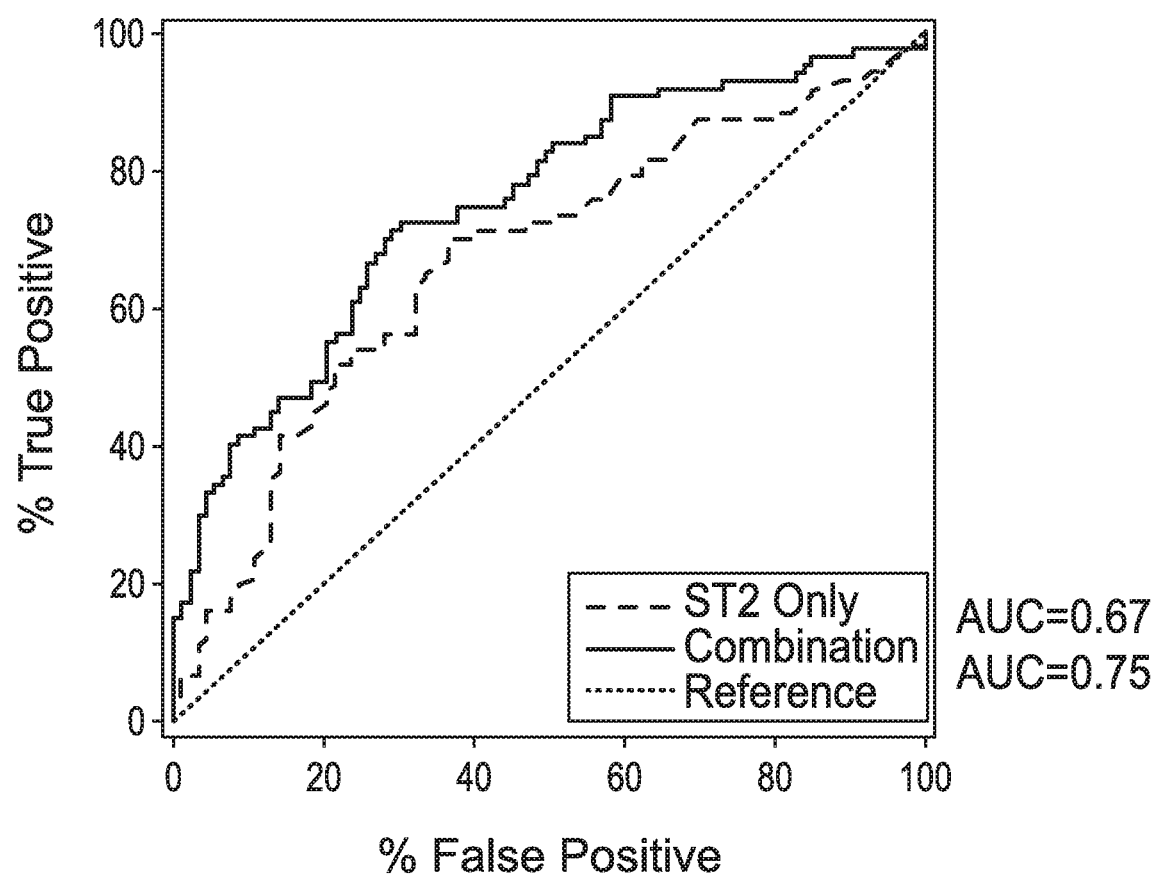
FIG. 4 depicts ROC curves for the best single biomarker and the combination model in verification cohort 2 as analyzed in Example 1. Particularly, ROC curves for the best single biomarker (ST2, dotted line, AUC=0.67) and the combination model (solid line, AUC=0.75) comparing patients with cGVHD (n=87) and time-matched controls without cGVHD (n=93).

To determine the best combination model, forward selection with a 0.05 significance threshold was used, confirmed by backward selection. Receiver operating characteristic (ROC) curves and area under the curve (AUC) were generated for the best single biomarker and the combination model (FIG. 4). Differences in cGVHD severity between groups were evaluated using the Wilcoxon two-sample tests. The analysis of NRM divided the panel weighted sum on the median value among cGVHD cases in both verification cohorts and compared cases above and below the median. NRM was estimated using cumulative incidence methods treating relapse as a competing risk.

Results

Discovery Study Using Quantitative Proteomics

Pooled plasma from 35 patients with cGVHD was labeled with one isobaric tag for relative and absolute quantitation with iTRAQ labeling (isobaric tags for relative and absolute quantification) and compared to pooled plasma from 18 patients without cGVHD, labeled with a different iTRAQ label.

The characteristics of patients in the cohorts are presented in Table 2.

TABLE 2

Patient and GVHD characteristics

| | | Discovery Cohort (n = 53) | | | Independent Verification Cohort 1 (n = 211) | | | Independent Verification Cohort 2 (n = 180)§‡ | | |
|---|---|---|---|---|---|---|---|---|---|---|
| | | cGVHD (n = 35) | Controls (n = 18) | P | cGVHD (n = 178) | Controls (n = 33) | P | cGVHD (n = 87) | Controls (n = 93) | P |
| | | | | | Age, years | | | | | |
| | median | 50 | 27 | 0.03 | 52 | 54 | 0.55 | 51 | 52 | 0.44 |
| | range | 6-67 | 1-66 | | 19-79 | 22-72 | | 21-78 | 20-71 | |

TABLE 2-continued

Patient and GVHD characteristics

| | Discovery Cohort (n = 53) | | | Independent Verification Cohort 1 (n = 211) | | | Independent Verification Cohort 2 (n = 180)§‡ | | |
|---|---|---|---|---|---|---|---|---|---|
| | cGVHD (n = 35) | Controls (n = 18) | P | cGVHD (n = 178) | Controls (n = 33) | P | cGVHD (n = 87) | Controls (n = 93) | P |
| Sex, n (%) | | | | | | | | | |
| Female | 11 (31) | 6 (33) | 1.00 | 77 (43) | 18 (55) | 0.23 | 49 (56) | 57 (61) | 0.50 |
| male | 24 (69) | 12 (67) | | 101 (57) | 15 (45) | | 38 (44) | 36 (39) | |
| Donor type and match, n (%) | | | | | | | | | |
| Matched sibling | 29 (83) | 17 (94) | 0.40 | 66 (37) | 18 (55) | 0.06 | 38 (44) | 36 (39) | 0.50 |
| Other* | 6 (17) | 1 (6) | | 112 (63) | 15 (45) | | 49 (56) | 57 (61) | |
| Stem cell source, n (%) | | | | | | | | | |
| PBSC | 28 (80) | 10 (56) | 0.11 | 161 (90) | 26 (79) | 0.05 | 77 (89) | 80 (86) | 0.62 |
| Other | 7 (20) | 8 (44) | | 17 (10) | 7 (21) | | 10 (11) | 13 (14) | |
| Conditioning regimen intensity, n (%) | | | | | | | | | |
| Myeloablative | 26 (74) | 13 (72) | 1.00 | 105 (59) | 19 (58) | 0.88 | 37 (43) | 41 (44) | 0.83 |
| Non Myeloablative | 9 (26) | 5 (28) | | 73 (41) | 14 (42) | | 50 (57) | 52 (56) | |
| Prior acute GVHD, n (%) | | | | | | | | | |
| Yes | 18 (51) | 0 (0) | 0.0001 | 135 (76) | 24 (73) | 0.70 | 36 (43) | 45 (51) | 0.35 |
| No | 17 (49) | 18 (100) | | 43 (34) | 9 (37) | | 47 (57) | 44 (49) | |
| Time post-HCT to cGVHD diagnosis, days | | | | | | | | | |
| Median | 119 | na | na | 210 | na | na | 203 | na | na |
| Range | 56-352 | na | | 38-1757 | na | | 86-461 | na | |
| Time post-HCT to sample acquisition, days | | | | | | | | | |
| Median | 103 | 102 | 0.03 | 391 | 369 | 0.84 | 236 | 192 | 0.63 |
| Range | 50-372 | 94-189 | | 192-1852 | 161-3641 | | 86-522 | 133-482 | |
| NIH global severity, n (%) | | | | | | | | | |
| Mild | 2 (6) | na | na | 13 (7) | na | na | 15 (18) | na | na |
| Moderate | 20 (57) | na | | 103 (58) | na | | 45 (55) | na | |
| Severe | 13 (37) | na | | 62 (35) | na | | 22 (27) | na | |
| Steroid use at time of sampling, n (%) | | | | | | | | | |
| Yes | 4 (11) | 0 (0) | 0.29 | 108 (610) | 2 (6) | <0.0001 | 51 (61) | 22 (24) | <0.0001 |
| No | 31 (89) | 18 (100) | | 70 (39) | 31 (94) | | 36 (39) | 71 (76) | | na: not applicable;
*other: only 4 cord blood cells transplant among the cases and none among the controls
§matched for age, sex, donor (matched sibling v. others), stem cell source, conditioning (myeloablative v. others), and time from HCT to sample collection from the U54 multicenter cohort.
‡8 patients missing data for prior acute GVHD, 4 cases missing data for NIH severity.

Patients in the cGVHD group were older and more likely to have had prior aGVHD than the controls without cGVHD. Otherwise, there were no statistically significant differences between the patients with cGVHD and without cGVHD according to sex, donor and HLA type, graft source, or conditioning intensity. Of note, samples were selected so that patients had minimal to no corticosteroid immunosuppression at the time of sampling in both cGVHD and control cases. Samples were collected at similar times for both the cGVHD cases and controls with a less extended range for controls, since the blood collection for controls occurred at regular visits, around day 100 and day 180 post-HCT. Samples were thus obtained at a median of 103 days (50-372 days) after HCT in the cGVHD group compared to 102 days (94-189 days) after HCT in the control group (p=0.03).

iTRAQ labels allow for comparison of relative concentrations of proteins between groups. Overall, 1998 proteins were identified and quantified, and 105 of these proteins were differentially expressed by at least a 1.25-fold difference that distinguished cGVHD patients from patients without cGVHD at the time of sampling. Antibodies suitable for enzyme-linked immunosorbent assays (ELISAs) were available for 22 of these proteins (Table 1), and chemokine (C—X—C motif) ligand 9 (CXCL9) and IL-1RL1 (also known as ST2) also were considered for validation.

Verification Cohort 1 and Biomarker Panel Development

The concentrations of the 26 identified proteins in samples from verification cohort 1, which consisted of 178 HCT patients with cGVHD and 33 HCT controls without cGVHD were measured. The patient and GVHD characteristics for the two groups are presented in Table 1 above. Patient sex and median age at the time of transplantation were similar between the two groups. There was a trend toward over-representation of unrelated donors in the cGVHD group. As expected, the use of peripheral blood stem cells (PBSCs) was a risk factor for cGVHD. The use of full-intensity conditioning was not a risk-factor for cGVHD. The incidence of prior aGVHD was similar in both groups in this cohort. According to the NIH global severity score, 7% of the patients had mild cGVHD, 58% had moderate cGVHD, and 35% had severe cGVHD. Plasma samples were collected at similar times from both cGVHD patients and controls: a median of 391 days (192-1852 days) after HCT in the cGVHD group compared to 369 days (161-3641 days) after HCT in the control group (p=0.84). Unlike the discovery cohort, 61% of the cGVHD patients were under corticosteroid treatment at the time of sampling, compared to 6% of control individuals (p<0.0001).

To create the biomarker panel, logistic regression was used to evaluate the associations between cGVHD and biomarkers after log transformation. All analyses of individual biomarkers were adjusted for the following seven clinical variables: age, sex, donor (matched sibling v. others), stem cell source (PBSC v. others), conditioning intensity (myeloablative v. others), prior aGVHD, and time from HCT to sample collection. Notably, only donor type (p=0.03) and PBSCs as the stem cell source (p=0.01) were significant in multivariate analysis. Of the 26 proteins tested, 9 were associated with cGVHD with a p-value<0.05. These included ST2, matrix metalloproteinase 3 (MMP3), tumor necrosis factor receptor superfamily member 10C (TNFRSF10C), osteopontin (OPN or SPP1), selectin P (SELP), human homolog of the proto-oncogene c-kit (C-KIT), cartilage oligomeric matrix protein (COMP), CXCL9, and melanoma cell adhesion molecule (MCAM or CD146) (Table 2). To determine the best combination model, unadjusted forward selection with a 0.05 significance threshold was used using these 9 markers, confirmed by backward selection. The selection procedure identified 4 proteins, ST2, MMP3, CXCL9, and OPN, for inclusion in the combination panel. The other 5 proteins were not included in the panel, because they did not show an additional effect in forward and backward selection models (Table 3).

TABLE 3

Biomarkers associated with cGVHD in verification cohort 1

| | AUC | P | Adjusted P | Combination[1] |
|---|---|---|---|---|
| ST2 | 0.832 | <0.0001 | <0.0001 | Yes |
| MMP3 | 0.787 | <0.0001 | <0.0001 | Yes |
| TRAILR3 | 0.716 | 0.0002 | 0.0002 | |
| OPN | 0.708 | <0.0001 | <0.0001 | Yes |
| SELP | 0.661 | 0.008 | 0.005 | |
| CKIT | 0.654 | 0.007 | 0.01 | |

TABLE 3-continued

Biomarkers associated with cGVHD in verification cohort 1

| | AUC | P | Adjusted P | Combination[1] |
|---|---|---|---|---|
| COMP | 0.643 | 0.009 | 0.002 | |
| CXCL9 | 0.628 | 0.02 | 0.01 | Yes |
| CD146 | 0.616 | 0.03 | 0.04 | |
| Combination1 | 0.885 | <0.0001 | <0.0001 | |

[1]Combination model includes ST2, MMP3, CXCL9, and OPN (via either forward or backward selection).

To better define the potential clinical utility of the four identified proteins, receiver operating characteristic (ROC) curves were generated for the best single biomarker and the combination model. The area under the ROC curve (AUC) for the four-biomarker panel was 0.89, while the AUC for ST2 was 0.83 (FIG. 1).

Predictive Significance of the Biomarker Panel for cGVHD Severity and NRM

Figure 2:
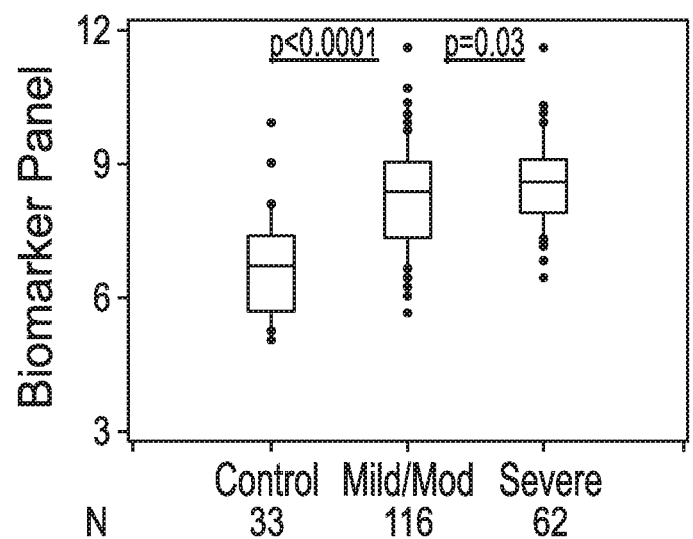
FIG. 2 depicts the association between biomarker panel and cGVHD severity in verification cohort 1 as analyzed in Example 1. Data are illustrated as box and whisker plots with the whiskers indicating the 90th and 10th percentiles. P-values compare controls v. patients with mild/moderate cGVHD, and patients with mild/moderate cGVHD v. those with severe cGVHD, according to Wilcoxon two-sample tests.

Next, the biomarker panel was evaluated as to whether it was associated with cGVHD severity. Very few patients had mild cGVHD, and thus, these patients were combined with those who presented with moderate cGVHD. Using Wilcoxon two-sample tests, the biomarker panel (defined with the following formula $3.23*\log_{10}ST2+1.81*\log_{10}CXCL9+1.64*\log_{10}MMP3+1.58*\log_{10}OPN$) was compared between groups with different cGVHD severity (none, mild/moderate, and severe). The severity of cGVHD was correlated with the biomarker panel [p<0.0001 comparing none with any cGVHD, and p=0.03 comparing mild/moderate with severe cGVHD (unadjusted), FIG. 2]. In regression analysis with adjustment for clinical variables, the p-value was 0.006 for mild/moderate versus severe cGVHD.

Figure 3:
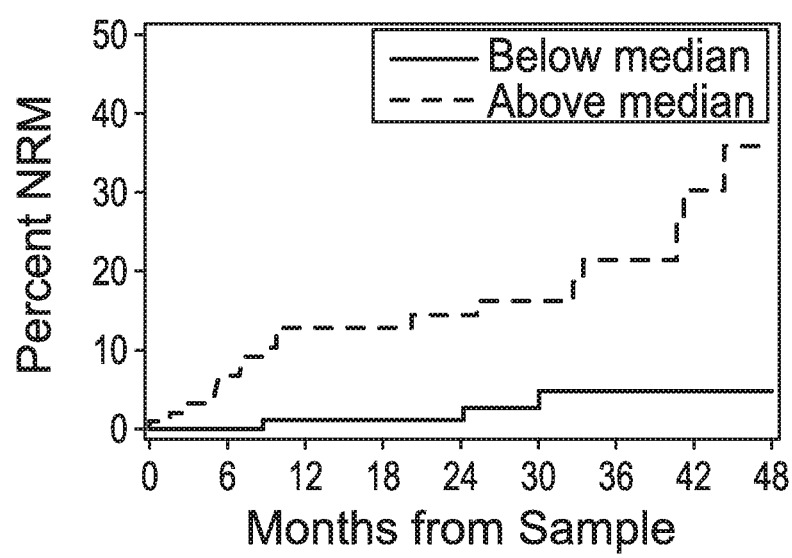
FIG. 3 depicts nonrelapse mortality (NRM) between groups with high versus low biomarker levels.

NRM was compared between groups with high versus low biomarker levels using a cutoff of the median value of the biomarker panel (median value obtained from the formula given above) among cGVHD cases. Patients with cGVHD and biomarker panel levels above the median had higher NRM with a hazard ratio (HR) of 7.0 (95% Cl, 2.0-24.8) and p-value of 0.003 after adjustment for the aforementioned clinical characteristics, compared with cGVHD patients with lower biomarker panel levels (FIG. 3).

Lastly, because the cohort consisted entirely of patients with multi-organ involvement, the biomarker panel was not associated with any specific target organ (Table 4).

TABLE 4

Verification cohort 1 biomarker panel according to cGVHD status and particular organ involvement

| | Median (range) | | | P-value | | | |
|---|---|---|---|---|---|---|---|
| | Control | cGVHD+ | | | cGVHD+ | | |
| Organ | (no cGVHD) | Organ− | Organ+ | Kruskal-Wallis | Organ+ vs. Organ− | Organ− vs Control | Organ+ vs Control |
| Skin | 10.0 (7.5-13.7) | 12.7 (7.8-19.1) | 12.8 (8.8-17.3) | <0.0001 | 0.58 | <0.0001 | <0.0001 |
| GI | 10.0 (7.5-13.7) | 12.6 (8.8-19.1) | 13.3 (7.8-17.3) | <0.0001 | 0.07 | <0.0001 | <0.0001 |
| Mouth | 10.0 (7.5-13.7) | 12.6 (9.0-19.1) | 12.8 (7.8-17.3) | <0.0001 | 0.99 | <0.0001 | <0.0001 |
| Eye | 10.0 (7.5-13.7) | 12.9 (8.8-19.1) | 12.6 (7.8-17.3) | <0.0001 | 0.37 | <0.0001 | <0.0001 |
| Lung | 10.0 (7.5-13.7) | 12.8 (7.8-17.3) | 12.7 (8.8-19.1) | <0.0001 | 0.46 | <0.0001 | <0.0001 |
| Liver | 10.0 (7.5-13.7) | 12.5 (7.8-16.6) | 13.1 (9.1-19.1) | <0.0001 | 0.003 | <0.0001 | <0.0001 |

| | N | | |
|---|---|---|---|
| | Control | cGVHD+ | |
| Organ | (No cGVHD) | Organ− | Organ+ |
| Skin | 33 | 65 | 113 |
| GI | 33 | 121 | 57 |
| Mouth | 33 | 67 | 111 |

TABLE 4-continued

Verification cohort 1 biomarker panel according to cGVHD status and particular organ involvement

| | | | |
|---|---|---|---|
| Eye | 33 | 97 | 81 |
| Lung | 33 | 61 | 116 |
| Liver | 33 | 97 | 80 |

Verification Cohort 2 from a Prospective Multicenter Consortium

The four-biomarker panel were then verified further in a second independent cohort of 180 patients who were matched for the following clinical characteristics: age, sex, donor (matched sibling v. others), stem cell source (mobilized peripheral blood stem cells v. others), conditioning (myeloablative v. others), and time from HCT to sample collection. These samples represent a subset of samples from a U54 consortium and included samples from the Fred Hutchinson Cancer Research Center (FHCRC), Dana-Farber Cancer Institute, University of Minnesota, the H. Lee Moffitt Cancer Center and Research Institute, Vanderbilt University Medical Center, Roswell Park Cancer Institute, Washington University St. Louis, and Cleveland Clinic. Patient and GVHD characteristics in the two groups are presented in Table 1 above. Patient characteristics in the chronic GVHD and control groups were similar because patients had been matched accordingly. However, compared to the first cohort, fewer patients in this cohort received full-intensity conditioning and fewer patients had previously experienced aGVHD. This cohort also included more patients with mild cGVHD (18% v. 7% in cohort 1) and fewer with severe cGVHD (27% v. 35% in cohort 1) according to the NIH Global severity score. The median day of sample collection was earlier than in the previous cohort at around 8 months and did not differ between groups. Similar to verification cohort 1, 61% of the cGVHD patients under corticosteroid treatment at time of sampling, but unlike verification cohort 1, 24% of the controls also were under corticosteroid treatment at the time of sampling (p<0.0001), which was adjusted for in the analysis.

Three of the four biomarkers included in the panel (ST2, CXCL9, and MMP3) were confirmed to be associated with cGVHD in this cohort, whereas OPN was not. The biomarker panel including all four markers had an AUC of 0.75 (p<0.0001; Table 5). The AUC using weights from the prior analysis was similar at 0.72 (p<0.0001; Table 5).

TABLE 5

Biomarkers associated with cGVHD in verification cohort 2

| | Area under ROC | P-value | Adjusted[1] P-value | Adjusted[3] P-value |
|---|---|---|---|---|
| ST2 | 0.671 | 0.0002 | <0.0001 | 0.02 |
| CXCL9 | 0.644 | 0.0009 | 0.0005 | 0.0001 |
| MMP3 | 0.661 | 0.0003 | 0.0001 | 0.09 |
| OPN | 0.534 | 0.66 | 0.47 | 0.98 |
| Combination | 0.752 | <0.0001 | <0.0001 | <0.0001 |
| Combination[2] | 0.720 | <0.0001 | <0.0001 | <0.0001 |

Figure 5:
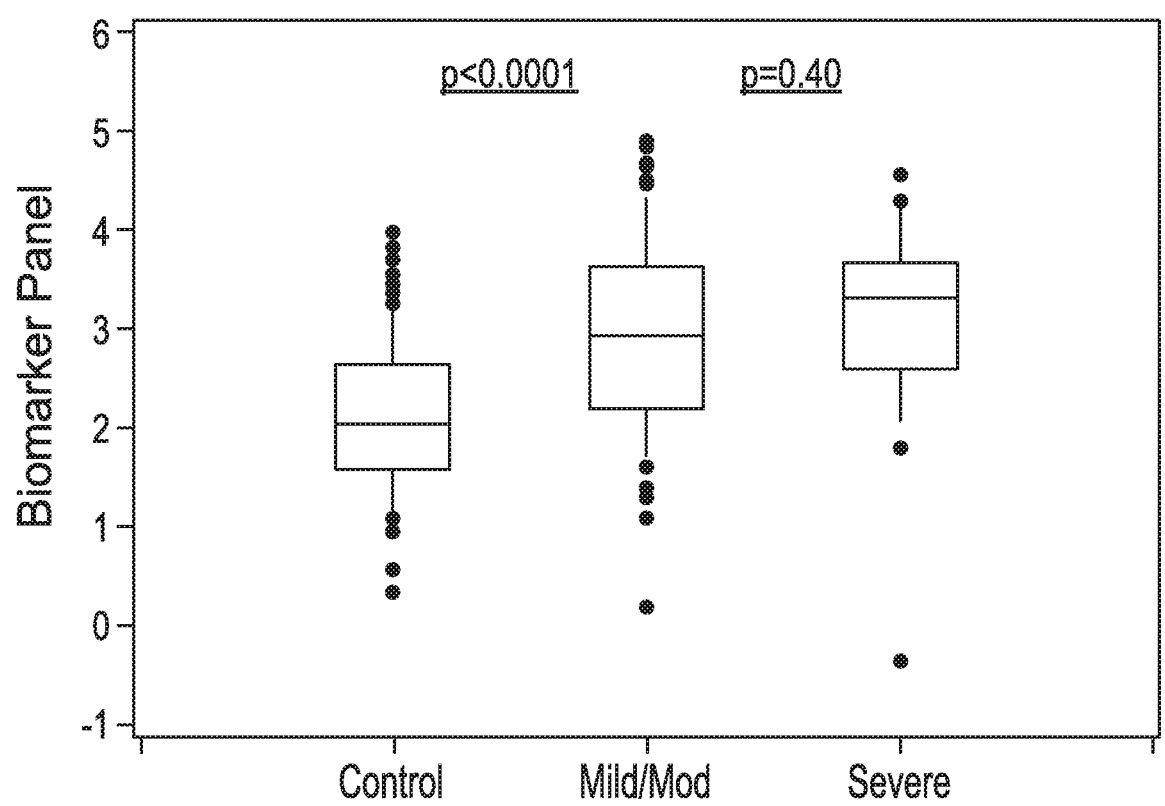
FIG. 5 depicts the association between biomarker panel and cGVHD severity in verification cohort 2 as analyzed in Example 1. Median value of the four-biomarker panel from controls (n=93), patients with mild/moderate cGVHD (n=61), and patients with severe cGVHD (n=22) in verification cohort 2. Data are illustrated as box and whisker plots with the whiskers indicating the 90th and 10th percentiles. P-values compare controls v. patients with mild/moderate cGVHD, and patients with mild/moderate cGVHD v. those with severe cGVHD, according to Wilcoxon two-sample tests.
Figure 6A:
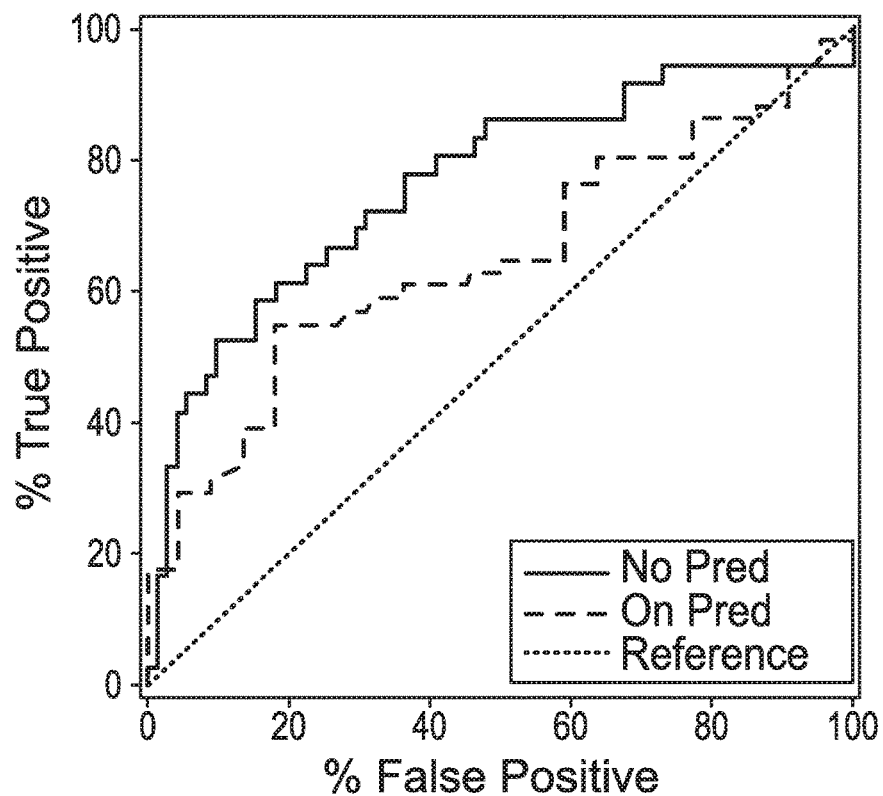
FIGS. 6A & 6B depict the utility of the biomarker panel being influenced by immunosuppression therapy and prior acute GVHD. Particularly.
Figure 6B:
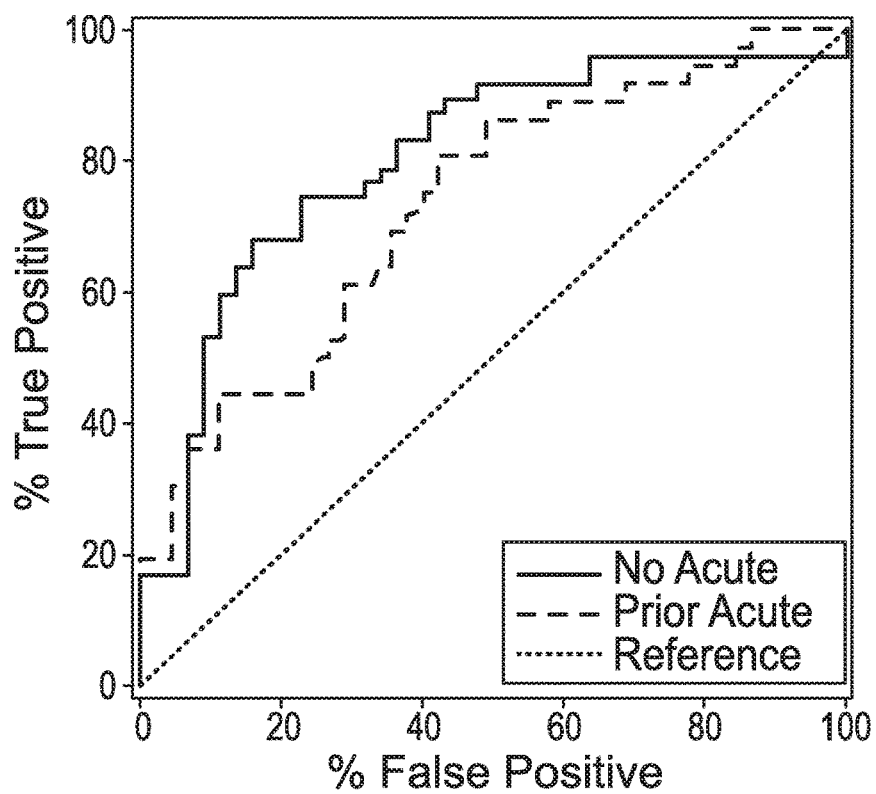

[1]adjusted for age, sex, stem cell source, conditioning, donor, aGVHD, time of sample collection post-HCT
[2]using weights from prior analysis
[3]additionally adjusted for prednisone use In this cohort, the biomarker panel was not significantly associated with a difference in severity of cGVHD (p=0.40; FIG. 5). NRM could not be evaluated because only three patients experienced NRM events among the cGVHD cases during the period of observation. Previously reported biomarkers for both acute and chronic GVHD have been shown to decrease after initiation of corticosteroid treatment, and 61% of cGVHD patients and 24% of controls were under systemic corticosteroid treatment at the time of sample acquisition. Therefore, the effect of corticosteroid treatment and prior aGVHD on the ability of the biomarker panel to distinguish patients with cGVHD from those without cGVHD was evaluated. As shown in FIG. 6A, the biomarker panel showed better performance when comparing patients who were not under treatment with corticosteroids. Similarly, the biomarker panel was better able to differentiate patients with cGVHD from those without cGVHD in the absence of prior aGVHD (FIG. 6B). Of note, all control patients under corticosteroid treatment were selected for the absence of active acute or chronic GVHD. Similar to verification cohort 1, cohort 2 consisted entirely of patients with multi-organ involvement, and thus, the biomarker panel was not associated with involvement of any specific target organ (Table 6).

TABLE 6

Verification cohort 2 biomarker panel according to cGVHD status and particular organ involvement

| | Median (range) | | | P-value | | | |
|---|---|---|---|---|---|---|---|
| | | | | | cGVHD+ | | |
| | Control | cGVHD+ | | Kruskal- | Organ+ | Organ− | Organ+ |
| Factor | (no cGVHD) | Organ− | Organ+ | Wallis | vs. Organ− | vs Control | vs Control |
| Skin | 2.04 (0.32-3.97) | 2.85 (0.19-4.69) | 3.08 (−0.34-4.84) | <0.0001 | 0.83 | <0.0001 | <0.0001 |
| GI | 2.04 (0.32-3.97) | 2.92 (−0.34-4.84) | 3.34 (0.19-4.92) | <0.0001 | 0.14 | <0.0001 | 0.0003 |
| Mouth | 2.04 (0.32-3.97) | 2.95 (1.11-4.84) | 2.97 (−0.34-4.92) | <0.0001 | 0.46 | <0.0001 | <0.0001 |
| Eye | 2.04 (0.32-3.97) | 3.00 (−0.34-4.69) | 2.95 (1.85-4.92) | <0.0001 | 0.19 | <0.0001 | <0.0001 |
| Lung | 2.04 (0.32-3.97) | 3.01 (1.30-4.92) | 2.89 (−0.34-4.56) | <0.0001 | 0.51 | <0.0001 | <0.0001 |
| Liver | 2.04 (0.32-3.97) | 2.82 (−0.34-4.92) | 3.02 (1.30-4.56) | <0.0001 | 0.35 | 0.0001 | <0.0001 |

TABLE 6-continued

Verification cohort 2 biomarker panel according to cGVHD status and particular organ involvement

| | N | | |
|---|---|---|---|
| | | cGVHD+ | |
| Factor | Control | Organ− | Organ+ |
| Skin | 93 | 39 | 44 |
| GI | 93 | 62 | 22 |
| Mouth | 93 | 37 | 48 |
| Eye | 93 | 51 | 33 |
| Lung | 93 | 42 | 40 |
| Liver | 93 | 41 | 41 |

Discussion

The discovery of valid and reproducible biomarkers for cGVHD remains a significant challenge. Compared to aGVHD, cGVHD is clinically more heterogeneous and can involve many more target organs, often simultaneously. In the present Example, unbiased large-scale tandem MS (MS/MS)—based analysis of plasma samples was performed that can quantify proteins at low concentrations to detect proteins of interest in the development of cGVHD. The initial approach to the identification of cGVHD biomarkers in patient plasma screened by competitive hybridization to arrays of antibodies specific for 131 diverse proteins could be considered internally unbiased because each antibody was represented at an equal level, but was inherently limited by the availability and selection of antibodies. In contrast, tandem MS/MS is a broader and less biased approach for analyzing complex proteomes present in samples such as plasma by matching mass spectra to a sequence database to identify proteins. Of note, the proteomics experiment involved a separate pool for newly diagnosed de novo cGVHD (with no previous acute GVHD) and progressive cGVHD (following unresolved acute GVHD), but the iTRAQ experiment did not show differences in the expression of candidate proteins between these two groups (data not shown).

Another major strength of the present Example was the ability to reproduce a strong correlation of the four-biomarker panel in a second verification cohort, which include samples from eight different sites, which is the current preferred requirement for the identification of "biomarkers" according to the 2014 NIH biomarker consensus (Paczesny et al., Journal of the Am. Soc. For Blood and Marrow Transplantation. 2015, 21(5):780-92). As shown in Table 3 above, using weights from the first cohort analysis, the biomarker panel had the ability to distinguish patients with and without cGVHD with a similar AUC. The strong correlation of biomarkers with cGVHD severity and NRM in the first verification cohort was much less impressive in the second verification cohort. Nonetheless, this biomarker panel may be clinically relevant for predicting worse outcomes. Serial measurements beyond days 80-100 post-HCT may identify high-risk patients for earlier intervention on a preemptive basis, a superior alternative to administration of prophylaxis to all patients.

The discovery approach highlighted some interesting biological pathways that may represent novel therapeutic avenues relevant to the three proteins that were increased in both verification cohorts. CXCL9 is a T helper type 1 (Th1) chemokine that has been shown to attract CXCR3+ CD4+ T cells in target organs and can be detected in the blood. Given the well-described relationship of CXCL9-CXCR3 in Th1-mediated disease states, it is speculated that the Th1 pathway may thus be important during severe cGVHD. Some therapies applied for aGVHD, such as bortezomib, inhibit T-cell chemotactic movements, decrease CXCR3 expression, decrease CXCL9 secretion by activated T cells in a murine model, and may prevent GVHD when used for prophylaxis. Other CXCL9 and CXCR3 inhibitors are under development, raising the possibility of testing these findings in future clinical trials.

Soluble ST2 (sST2) is secreted by intestinal stromal/endothelial cells and T cells during aGVHD in experimental models, and ST2 blockade reduces the numbers of sST2-producing T cells while maintaining the numbers of protective membrane (m)ST2-expressing T cells during GVHD. It has now been shown that an elevated plasma level of sST2 in HCT patients is a risk factor for severe GVHD and death, which is why ST2 was included with the candidate proteins identified by the proteomics analysis. Further experiments are needed to determine the effects of ST2 blockade in cGVHD models.

Figure 7:
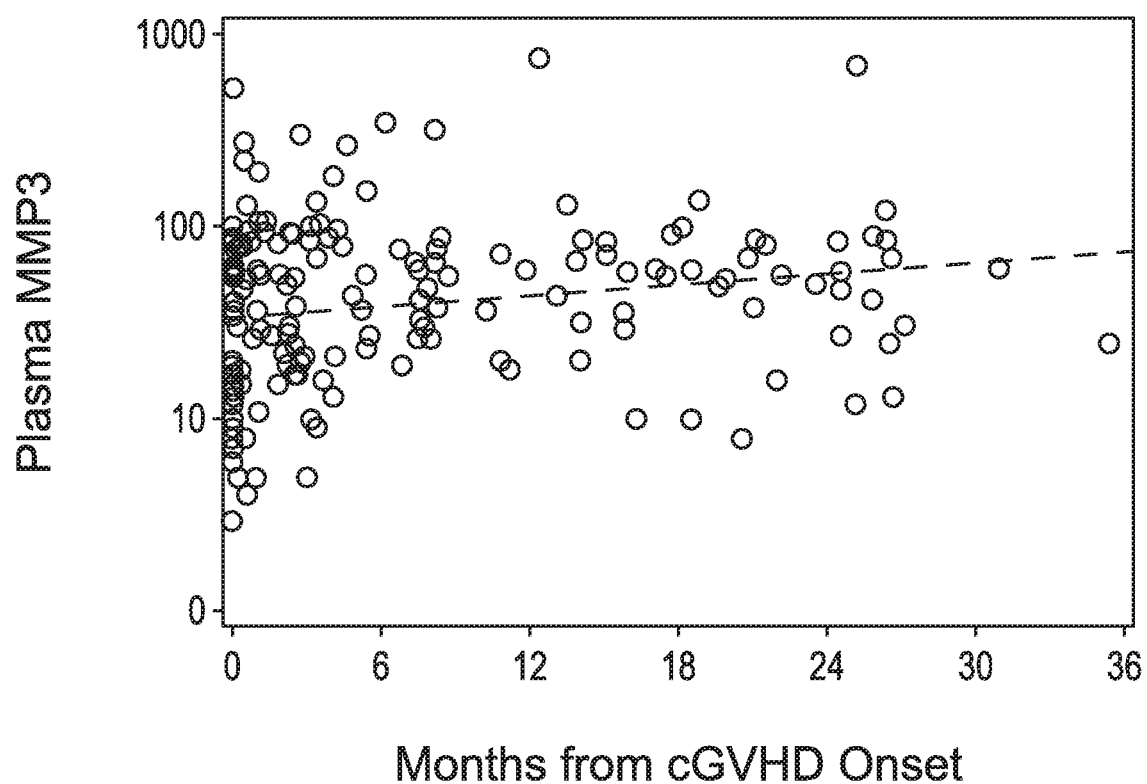
FIG. 7 depicts plasma MMP3 concentrations from time of cGVHD onset in verification cohort 1. Plasma MMP3 concentrations from time to cGVHD onset in patients with cGVHD in verification cohort 1 (n=178). Dashed line is estimated fit from linear regression model (p=0.009).

MMPs are prominent contributors to microenvironmental signals, because these proteolytic enzymes degrade structural components of the extracellular matrix (ECM), permitting tissue remodeling. Additionally, MMPs can release cell-bound inactive precursor forms of growth factors, degrade cell—cell and cell—ECM adhesion molecules, activate precursor zymogen forms of other MMPs, and inactivate inhibitors of MMPs and other proteases. MMP3 in particular has been shown to promote the epithelial-mesenchymal transition (EMT), potentially leading to tissue fibrosis. Opposite to the three other markers that were found at high levels early in the cGVHD course, MMP3 plasma concentrations seemed to increase over time from cGVHD onset (FIG. 7), suggesting that MMP3 is indeed involved in EMT and fibrosis. Targeted therapy with inhibitors of this pathway may be effective for established lesions.

Example 2

In this Example, mass spectrometry-based proteomic analysis was conducted similar to Example 1 with the exception of analyzing plasma pooled from patients 100 days from HCT.

In a multivariable model, the prognostic ability of the biomarker panel when measured at day 100 post-HCT in plasma of 161 patients from the verification cohort 2 of Example 1 was evaluated. Plasma concentrations of ST2 and CXCL9 measured at day 100 post-HCT, 3 months on average before the first clinical signs of cGVHD, were associated with future occurrence of cGVHD independent of known clinical risk factors including age, sex, stem cell source, conditioning, donor, and acute GVHD. Of note, significant association of day 100 plasma proteins with cGVHD within 6 months or at any time after day 100 was not seen. Furthermore, the AUC with aGVHD status only was 0.63, suggesting that the other clinical covariates are explaining the AUC of 0.73 for the clinical covariates in verification cohort 2. Although steroid use at day 100 was correlated with prior aGVHD, as one would expect, it was not at all prognostic for the future development of cGVHD. The results are shown below.

TABLE 7

Association of day 100 Biomarker levels with subsequent cGVHD (n = 172 patients)

| Model | Within 3 months (37 events) | | | Within 6 months (59 events) | | | Within 1 year (81 events) | | |
|---|---|---|---|---|---|---|---|---|---|
| | HR[1] (95% CI) | P | AUC[2] | HR[1] (95% CI) | P | AUC[2] | HR[1] (95% CI) | P | AUC[2] |
| Single biomarkers | | | | | | | | | |
| ST2 | 1.45 (0.6-3.3) | 0.38 | 0.54 | 0.86 (0.4-1.7) | 0.66 | 0.49 | 1.04 (0.6-1.8) | 0.91 | 0.54 |
| CXCL9 | 2.88 (1.5-5.7) | 0.0005 | 0.66 | 1.44 (1.0-2.2) | 0.06 | 0.53 | 1.46 (1.0-2.1) | 0.03 | 0.57 |
| MMP3 | 0.89 (0.3-2.3) | 0.81 | 0.52 | 0.99 (0.5-2.1) | 0.98 | 0.53 | 1.15 (0.6-2.2) | 0.67 | 0.56 |
| OPN | 1.00 (0.2-5.4) | 0.99 | — | 2.03 (0.5-7.8) | 0.30 | 0.57 | 1.54 (0.5-4.8) | 0.46 | 0.53 |
| Combination of biomarkers | | | | | | | | | |
| ST2 | 1.85 (0.6-5.7) | 0.009 | 0.67 | 0.68 (0.3-1.6) | 0.27 | 0.61 | 0.87 (0.4-18) | 0.22 | 0.60 |
| CXCL9 | 2.81 (1.4-5.6) | | | 1.43 (0.9-2.2) | | | 1.45 (1.0-2.1) | | |
| MMP3 | 0.67 (0.2-2.2) | | | 1.21 (0.5-3.0) | | | 1.28 (0.6-2.9) | | |
| OPN | 0.54 (0.1-3.5) | | | 2.43 (0.6-10.5) | | | 1.50 (0.4-5.1) | | |
| Single biomarkers with for clinical covariates | | | | | | | | | |
| ST2 | 3.91 (1.3-11.6) | 0.01 | 0.76 | 1.66 (0.7-4.0) | 0.26 | 0.67 | 1.47 (0.7-3.1) | 0.30 | 0.64 |
| CXCL9 | 3.10 (1.5-6.3) | 0.0002 | 0.77 | 1.47 (1.0-2.2) | 0.05 | 0.67 | 1.49 (1.1-2.1) | 0.02 | 0.64 |
| MMP3 | 1.56 (0.5-5.4) | 0.49 | 0.73 | 2.30 (0.8-6.4) | 0.11 | 0.70 | 1.96 (0.8-4.9) | 0.15 | 0.65 |
| OPN | 2.66 (0.5-14.5) | 0.26 | 0.73 | 4.34 (1.1-17.6) | 0.04 | 0.71 | 2.47 (0.8-7.9) | 0.13 | 0.65 |
| Combination of biomarkers with clinical covariates | | | | | | | | | |
| ST2 | 3.22 (0.9-11.8) | 0.001 | 0.79[3] | 1.02 (0.4-2.7) | 0.06 | 0.72[3] | 1.07 (0.5-2.4) | 0.05 | 0.67[3] |
| CXCL9 | 2.92 (1.4-6.1) | | | 1.46 (1.0-2.2) | | | 1.49 (1.1-2.1) | | |
| MMP3 | 1.19 (0.3-4.3) | | | 1.89 (0.6-5.7) | | | 1.79 (0.7-4.8) | | |
| OPN | 0.68 (0.1-4.7) | | | 3.06 (0.7-13.8) | | | 1.88 (0.5-6.7) | | |

[1]adjusted for age, sex, stem cell source, conditioning, donor, acute GVHD (8 patients excluded because of unknown aGVHD status).

In summary, this Example shows that the identified biomarker panel (particularly ST2 and CXCL9) measured prior to the clinical signs of cGVHD, and within 3 months after day 100, may improve stratification for risk of cGVHD and be used for future preemptive trials.

Based on the foregoing, it is concluded that the combination of plasma concentrations of ST2, CXCL9, and MMP3 represents a biomarker panel for non-invasive identification of cGVHD as verified in two independent cohorts. The biomarker panel also was associated with cGVHD severity and prediction of NRM. Furthermore, the identified markers represent several pathways, including T-cell activation and trafficking, endothelial injury, and tissue remodeling, which may provide opportunities for novel therapeutic interventions. Importantly, the biomarker panel was better able to distinguish patients with cGVHD from those without cGVHD in the absence of systemic corticosteroid therapy and any prior aGVHD.

What is claimed is:
1. A method of detecting the expression level of a biomarker panel in a subject receiving hematopoietic cell transplantation (HCT), the method comprising
measuring, in a biological sample from the subject, the expression of the biomarker panel comprising the biomarkers IL-1RL1, chemokine ligand 9 (CXCL9), matrix metalloproteinase-3 (MMP3), and osteopontin (OPN) by contacting the biological sample obtained from the subject with a first agent that specifically binds to IL-1RL1, a second agent that specifically binds to CXCL9, a third agent that specifically binds to MMP3, and a fourth agent that specifically binds to OPN, wherein each of said first, second, third and fourth binding agents forms a complex with its respective biomarker; and
detecting the agent-biomarker complexes, thereby determining the biomarker panel expression level.
2. The method of claim 1 wherein the biological sample is obtained from day 100 to day 180 from HCT.
3. A method of detecting the expression level of a biomarker panel comprising biomarkers IL-1RL1, chemokine ligand 9 (CXCL9), and matrix metalloproteinase-3 (MMP3), in a subject receiving hematopoietic cell transplantation (HCT), the method comprising
measuring in a biological sample from the subject the expression of the biomarkers by contacting the biological sample obtained from the subject with an antibody that specifically binds to IL-1RL1, an antibody that specifically binds to CXCL9, and an antibody that specifically binds to MMP3; and
detecting antibody-biomarker complexes formed, thereby determining the expression level of the biomarkers of the biomarker panel.
4. The method of claim 3 further comprising the step of detecting the expression level of the biomarker osteopontin (OPN) by contacting the biological sample obtained from the subject with an antibody that specifically binds to OPN.
5. A kit for detecting the expression level of a biomarker panel in a subject receiving hematopoietic stem cell transplantation (HCT), wherein reagents of said kit consist of
a first antibody that specifically binds to IL-1RL1, a second antibody that specifically binds to CXCL9, and a third antibody that specifically binds to MMP3.

* * * * *